United States Patent
Pohan

(10) Patent No.: US 9,952,338 B2
(45) Date of Patent: Apr. 24, 2018

(54) X-RAY DETECTOR FOR A COMPUTED TOMOGRAPHY SYSTEM

(71) Applicant: Siemens Aktiengesellschaft, Munich (DE)

(72) Inventor: Claus Pohan, Baiersdorf (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 14/666,441

(22) Filed: Mar. 24, 2015

(65) Prior Publication Data

US 2015/0276951 A1 Oct. 1, 2015

(30) Foreign Application Priority Data

Mar. 27, 2014 (DE) .................. 10 2014 205 735

(51) Int. Cl.
| | |
|---|---|
| *G01T 7/00* | (2006.01) |
| *G01N 23/04* | (2018.01) |
| *G01T 1/16* | (2006.01) |
| *G01T 1/29* | (2006.01) |

(52) U.S. Cl.
CPC ............ *G01T 7/00* (2013.01); *G01N 23/046* (2013.01); *G01T 1/16* (2013.01); *G01T 1/2985* (2013.01)

(58) Field of Classification Search
CPC ........... G01T 7/00; G01T 1/2985; G01T 1/16; G01N 23/046
See application file for complete search history.

(56) References Cited

U.S. PATENT DOCUMENTS

| | | | |
|---|---|---|---|
| 4,338,521 A | 7/1982 | Shaw et al. | |
| 5,142,559 A | * 8/1992 | Wielopolski | A61B 6/08 250/492.3 |
| 5,487,098 A | 1/1996 | Dobbs et al. | |
| 5,991,357 A | 11/1999 | Marcovici et al. | |

(Continued)

FOREIGN PATENT DOCUMENTS

| | | |
|---|---|---|
| DE | 19581491 T1 | 6/1997 |
| DE | 102009022264 B3 | 8/2010 |

(Continued)

OTHER PUBLICATIONS

EQ Series Angle Brackets. Newport catalog pp. 735-736 [online]. Newport Corporation, 2010 [retrieved on Sep. 27, 2016]. Retrieved from the Internet: <URL: web.archive.org/web/20100103200520/ http://newport.com/EQ-Series-Angle-Brackets/144479/1033/catalog.aspx#>.*

(Continued)

*Primary Examiner* — David Porta
*Assistant Examiner* — Shun Lee
(74) *Attorney, Agent, or Firm* — Harness, Dickey & Pierce, P.L.C.

(57) ABSTRACT

An x-ray detector is disclosed, for a computed tomography system. In an embodiment, the x-ray detector includes a base plate and a number of detector modules, each including at least one detector field with a detector surface facing counter to an r-direction on a front face and each including a module support, fastened to the base plate. In at least one embodiment, the module support includes a bearing surface facing the base plate, perpendicular to the detector surface, for fastening purposes.

13 Claims, 3 Drawing Sheets

(56) References Cited

U.S. PATENT DOCUMENTS

| | | | |
|---|---|---|---|
| 6,712,655 B1* | 3/2004 | Schlemmer | B63H 21/305 440/111 |
| 2003/0185338 A1* | 10/2003 | Dafni | A61B 6/56 378/15 |
| 2006/0126782 A1 | 6/2006 | Pohan et al. | |
| 2013/0114786 A1* | 5/2013 | Ikhlef | A61B 6/032 378/19 |
| 2013/0306877 A1 | 11/2013 | Pohan | |
| 2015/0071401 A1* | 3/2015 | Lacey | G01N 23/046 378/19 |

FOREIGN PATENT DOCUMENTS

| | | |
|---|---|---|
| DE | 102012213814 A1 | 2/2014 |
| DE | 112014004057 T5 | 6/2016 |

OTHER PUBLICATIONS

Jianyu, Wang et al; "Intelligent Building Security System Construction"; pp. 1-5; relevant claims: 1-11; ISBN: 978-7-5123-3013-9; 2012.

Jixiang, Zhong et al; "Intelligent Building Construction"; pp. 1-4; relevant claims: 1-11; ISBN: 978-7-118-05582-5; 2008.

* cited by examiner

X-RAY DETECTOR FOR A COMPUTED TOMOGRAPHY SYSTEM

PRIORITY STATEMENT

The present application hereby claims priority under 35 U.S.C. § 119 to German patent application number DE 102014205735.3 filed Mar. 27, 2014, the entire contents of which are hereby incorporated herein by reference.

FIELD

At least one embodiment of the invention generally relates to an x-ray detector for a computed tomography system, having a base plate, to which a number of module supports are fastened, each having at least one detector module facing in the direction of an x-ray radiation source.

BACKGROUND

An x-ray detector is known for example from DE 10 2012 213 814 A1, which originates from the applicant. This discloses an x-ray detector, which comprises a number of detector modules arranged next to one another in a stacking direction, said detector modules having a front face, which is aligned toward an x-ray radiation source during operation. In the first approximation the x-ray radiation source is punctiform and emits an essentially fan-shaped beam for the examination of an object (for example a patient). This beam passes through the object in a predetermined plane and finally strikes the detector modules. Each of said detector modules comprises a number of detector elements, having a detector surface with an associated surface normal.

In order to achieve an optimum signal strength, each of the detector modules is aligned in such a manner that the surface normal of the detector surface faces as far as possible in the direction of the x-ray radiation source. In combination with the fan-shaped beam this produces an arced arrangement of the detector modules. To achieve such an arrangement, a frame or support is provided, having a base plate with a curved mounting surface, to which the detector modules are fastened in a radial direction in relation to the x-ray radiation source. In other words, the detector modules are each mounted on the base plate in a mounting direction that corresponds to the surface normal of the respective detector module. The production of such a support is complex. Also the x-ray detector is typically exposed to significant centrifugal force during operation. The support is therefore designed as solid, with the result that its manufacture is resource-intensive.

SUMMARY

At least one embodiment of the invention is directed to an improved x-ray detector, which is stable and simple to manufacture.

According to at least one embodiment of the invention, an x-ray detector is disclosed. Advantageous embodiments, developments and variants are the subject matter of the subclaims.

In an embodiment, an x-ray detector for a computed tomography system includes a base plate and a number of detector modules. Each of these has at least one detector field with a detector surface facing counter to an r-direction on a front face. The r-direction here typically faces out from an x-ray radiation source of the computed tomography system in the direction of the x-ray detector. The detector modules also each comprise a module support, which is fastened to the base plate and to this end has a bearing surface facing the base plate, which is perpendicular to the detector surface. Perpendicular here and in particular also in the following means that two surfaces, two directions or a surface and a direction are at an angle of around 90° to one another. This angle is preferably greater than 80° and smaller than 100°, particularly as the detector surface is possibly positioned slightly obliquely or even in an inclined manner, for example due to the structure.

When the module support is mounted on the base plate, two surfaces are typically first brought into contact, for example by placing them on top of one another or resting them against one another. In other words, the bearing surface of the module support rests against the base plate. For example the base plate has an upper face (or surface) and the bearing surface is brought up against the upper face, in other words in particular the module support is positioned on the base plate. This means that the upper face and the bearing surface are arranged in particular parallel to one another.

BRIEF DESCRIPTION OF THE DRAWINGS

An example embodiment of the invention is described in more detail below with reference to the drawings, in which.

DETAILED DESCRIPTION OF THE EXAMPLE EMBODIMENTS

Figure 1:
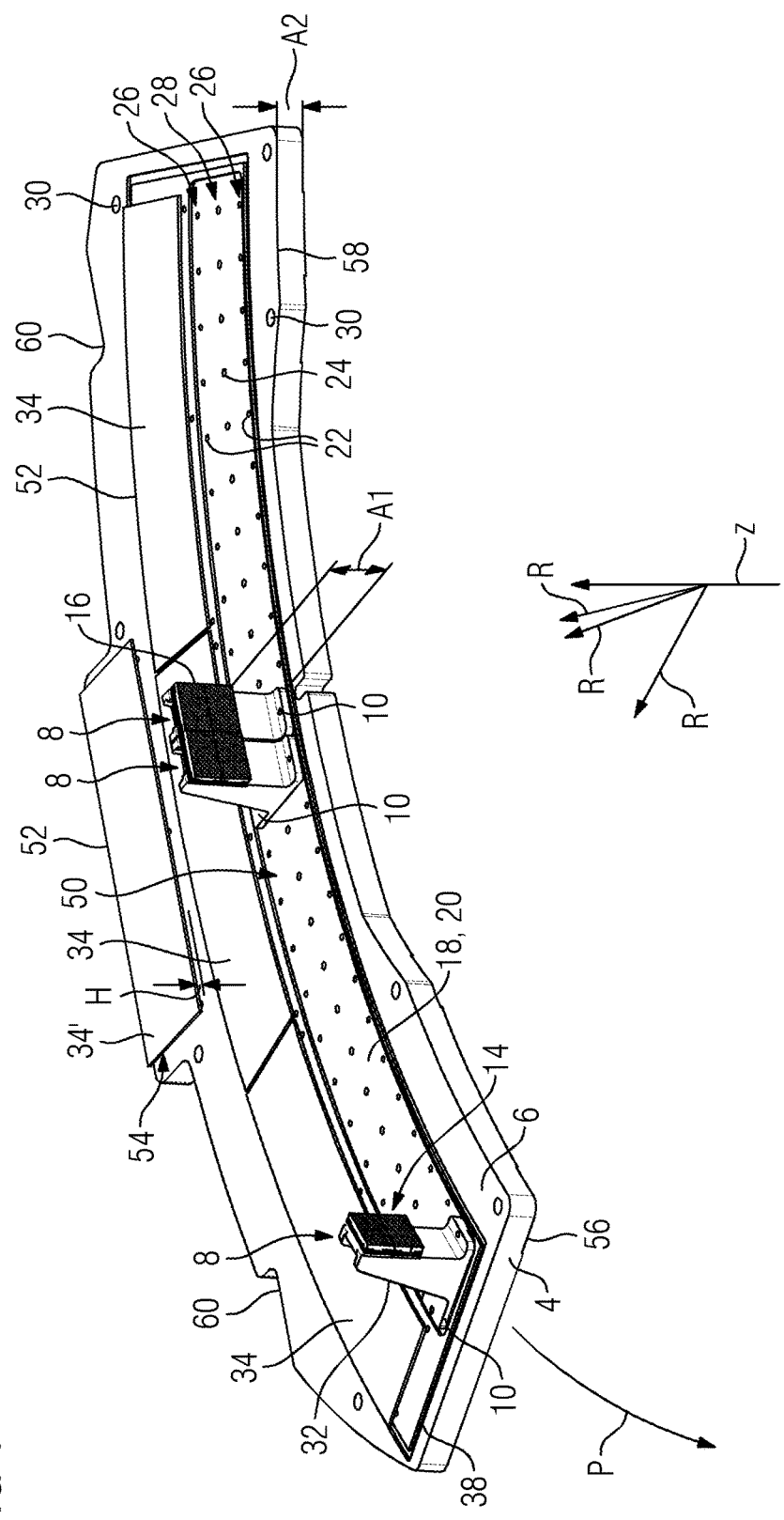
FIG. 1 shows a perspective view of an x-ray detector in an intermediate mounting position with a base plate and a number of detector modules.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In an embodiment, an x-ray detector for a computed tomography system includes a base plate and a number of detector modules. Each of these has at least one detector field with a detector surface facing counter to an r-direction on a front face. The r-direction here typically faces out from an x-ray radiation source of the computed tomography system in the direction of the x-ray detector. The detector modules also each comprise a module support, which is fastened to the base plate and to this end has a bearing surface facing the base plate, which is perpendicular to the detector surface. Perpendicular here and in particular also in the following means that two surfaces, two directions or a surface and a direction are at an angle of around 90° to one another. This angle is preferably greater than 80° and smaller than 100°, particularly as the detector surface is possibly positioned slightly obliquely or even in an inclined manner, for example due to the structure.

When the module support is mounted on the base plate, two surfaces are typically first brought into contact, for example by placing them on top of one another or resting them against one another. In other words, the bearing surface of the module support rests against the base plate. For example the base plate has an upper face (or surface) and the bearing surface is brought up against the upper face, in other words in particular the module support is positioned on the base plate. This means that the upper face and the bearing surface are arranged in particular parallel to one another.

In addition to such arrangement, the module support is preferably fastened to the base plate. In particular each module support has a mounting direction. If for example a screw connection using a screw is provided for fastening purposes, the screw has a longitudinal axis, which is parallel to a screwing direction. The screwing direction then corresponds to the mounting direction. In other words, the mounting direction refers to a direction in which the mounting, in particular the fastening, of the module support on the base plate is performed.

The x-ray detector is typically mounted on a rotating ring that can be rotated about a rotation axis. The rotation axis here faces in a direction referred to in the following as the z-direction. A direction perpendicular to the z-direction is referred to in the following as an r-direction. There are therefore a number of r-directions for the one z-direction.

According to the prior art, the module supports of an x-ray detector are each mounted in an r-direction. In other words, the respective mounting direction is the respective r-direction. As there are a number of r-directions, which are in particular not parallel to one another, the module supports are mounted on a correspondingly curved upper face (or surface). The curvature here follows a circumferential direction referred to in the following as the phi-direction, which is in particular perpendicular to the z-direction. One advantage achieved with the invention is in particular that an x-ray detector has at least one detector module that is mounted in the z-direction. All the detector modules of the x-ray detector are preferably mounted in the z-direction. In other words, the mounting direction is the z-direction. The bearing surface is also expediently perpendicular to the z-direction. In particular the mounting direction is perpendicular to the r-direction.

To mount a number of module supports on a common base plate, the base plate can advantageously be embodied with an essentially planar, in other words not curved, upper face. In other words, fastening to a curved surface is advantageously avoided.

According to the prior art, the mounting direction of each detector module is also essentially parallel to the surface normal of the detector field positioned on the module support. The curved upper face already described above, on which a number of such module supports are positioned, disadvantageously results in particular from the plurality of mounting directions. As the detector surfaces are arranged in an arc in the phi-direction, a correspondingly individual mounting direction, corresponding in each instance to an r-direction, results for each detector module. Therefore in the prior art the mounting directions differ, disadvantageously requiring a curved upper face for mounting. This disadvantage is eliminated according to the invention in that the mounting direction is expediently the z-direction and therefore all the detector modules of the x-ray detector preferably have the same mounting direction. The upper face, on which said detector modules are mounted, therefore does not have to be curved but can expediently be embodied as planar. This particularly simplifies the manufacture of the x-ray detector.

The detector fields are designed to detect x-ray radiation and to this end comprise a number of individual detector elements or sensors, which are arranged in a matrix. The detector elements of a detector field all face essentially in the same direction and thus form the detector surface on the front face, said detector surface in particular facing the x-ray radiation source. As this is approximately punctiform, an individual detector element does not necessarily face exactly in the direction of the x-ray radiation source.

The module support is advantageously configured as L-shaped or T-shaped, with a plinth (or foot or base), which comprises the bearing surface in particular. Connected to the plinth in particular is a wall standing thereon, which has a wall front face and a wall rear face. The wall preferably extends essentially in the z-direction. The plinth and wall are suitably perpendicular to one another. The term perpendicular here should in particular also be understood as mentioned above. The detector field is positioned on or fastened to the wall front face, which is preferably perpendicular to the r-direction. This means that the detector field is advantageously aligned in the r-direction.

The module support is preferably manufactured as a single piece. This means that the module support is particularly simple to manufacture.

During operation, the detector field absorbs x-ray radiation allowing it to generate a signal, which can preferably be forwarded for example to an electronic unit positioned on the x-ray detector by means of a connector of the detector field. To this end at least one cutout for the passage of the connector is advantageously incorporated in the module support. The cutout is incorporated in the wall for example in such a manner that the connector is introduced into the cutout and can be connected correspondingly on the rear face and/or can be connected for example to the electronic unit. In particular it is possible for a number of detector fields to be positioned on a module support and for a number of cutouts to be incorporated therein in order to connect and/or link the detector fields in a suitable manner.

During operation, the x-ray detector is possibly exposed to significant centrifugal force and/or other mechanical loads. To improve mechanical stability the module support preferably has a number of stays or bracing bars. These are connected to the wall and plinth in a suitable manner. In particular the stays, the wall and the plinth are configured as a single part. This ensures in particular that the module support has good stability.

In one suitable embodiment, the module support has two stays, which form a U-shaped profile with the bearing surface. For example two stays extend from the plinth and along the wall. The stays therefore form a U-shaped profile with the plinth. In an alternative embodiment only one stay extends from the plinth in this manner, forming a T-shaped profile therewith.

The base plate comprises an upper and lower face, which are advantageously embodied as essentially planar, in other words they are in particular not curved surfaces. This means in particular that the upper and lower face are perpendicular to the z-direction. Recesses, milled out regions and/or channels are also provided in a suitable manner for example for guidance and/or as stop surfaces for the module supports. An essentially planar surface then means in particular that such structuring is incorporated in the surface. Such an essentially planar surface, in other words the upper and/or lower face as well, has a border that can arc in the phi-direction.

Upper and lower face are preferably parallel to one another, which allows the base plate to be manufactured relatively simply. The base plate is preferably manufactured as a single piece.

The module supports are preferably arranged on the base plate in an arc, preferably in the phi-direction and in particular on a fastening plane. To this end the base plate advantageously has a recess that arcs in the phi-direction or even a depression on the upper face. The depression here forms a depression base, which is in particular planar.

The module support is fastened to the base plate in a suitable manner by means of a screw connection, with the result that the module support and the base plate are connected in a particularly stable manner. To this end the module support advantageously has at least one through hole preferably configured as a drilled hole and the base plate has a threaded hole associated with the through hole. A screw is then screwed into the thread through the through hole to fasten the module support.

The base plate advantageously has a number of further through holes, which are preferably also configured as drilled holes, in particular to fasten the x-ray detector to the computed tomography system. This means that the x-ray detector can be positioned on the computed tomography system, for example by way of a screw connection.

In order to arrange the module support on the base plate in a suitable manner, in one preferred embodiment a number of positioning elements are provided both on the base plate and on the module support. This in particular allows each module support to be fastened with just one fastening element, at the same time ensuring a correct arrangement. In one preferred embodiment each of the positioning elements is a drilled hole, with at least one such drilled hole in the module support lying flush with a drilled hole in the base plate. When the x-ray detector is mounted, it is then possible to align the module support in a suitable manner by means of a positioning pin before it is fastened. To this end the positioning pin is inserted into a drilled hole in the module support and into a drilled hole in the base plate. To produce an arced arrangement the positioning elements of the base plate are preferably arranged on one or more arced lines, preferably in the phi-direction. These preferably run in the fastening plane.

The x-ray detector advantageously has a cover with a rear wall, which is arranged on the rear face of the x-ray detector. This in particular allows the escape of x-ray radiation that has not been absorbed by detector elements to be avoided. To this end the rear wall advantageously extends in the z-direction and the phi-direction. The cover is suitably connected to the base plate in a thermally conducting manner, with the result that heat produced in particular by absorbed x-ray radiation can be dissipated efficiently.

The cover is expediently fastened to the base plate by means of a number of fastening elements and encloses a cover region in particular in combination with the base plate. In particular the cover does not have a front wall, in other words it is open counter to the r-direction. In this region however the cover region is preferably covered by an in particular light-tight material that allows the greatest possible passage of x-ray radiation in the r-direction, for example by a shield made of black-colored plastic. The detector modules are then preferably housed in particular in the cover region and in particular behind the shield in the r-direction.

In one advantageous embodiment the x-ray detector has a number of electronic unit components, which are arranged on the base plate and within and/or outside the cover region. These electronic unit components serve for example to bring about the abovementioned electronic unit for evaluating detector signals. An electronic unit component preferably comprises an electronic power unit. The arrangement on the base plate in particular ensures efficient heat dissipation.

The electronic unit components are preferably embodied in a flat manner, for example in the form of a so-called flat module. This means that the height of each of the electronic unit components is low compared with the height of the detector modules. The detector surfaces are expediently arranged at a defined distance from the base plate and the height of the electronic unit components is lower than this distance. The electronic unit components preferably each comprise a board, which extends essentially in the r-direction and the phi-direction. The height of the electronic unit components then extends in particular in the z-direction. The low height in particular ensures that the electronic unit components only have a small cross section in relation to the x-ray source and therefore are struck to the smallest possible degree by x-ray radiation.

The electronic unit components are preferably also each covered by a shield. This shield extends over the respective electronic unit component in the r-direction and the phi-direction in such a manner that said electronic unit component is arranged essentially in a space formed by the shield and the base plate. The shield is fastened to the base plate in a suitable manner and is in particular connected thereto in a thermally conducting manner.

An x-ray detector 2 according to FIG. 1 is provided in particular for use in a computed tomography system (not shown in detail here). The x-ray detector 2 comprises a base plate 4 with an upper face 6, to which a number of detector modules 8 are fastened. The x-ray detector 2 shown in FIG. 1 is designed to hold twenty four detector modules 8 but only three detector modules 8 are shown for greater clarity. Alternatively a different number of detector modules 8 are provided. These each comprise a module support 10 and a number of detector fields 12. They are positioned on a front face 14 of the respective detector module 8. In the example embodiment illustrated here each of the detector modules 8 comprises two detector fields 12, which together form a detector surface 16.

The detector fields 12 and therefore also the detector surfaces 16 each face in an r-direction R and in the direction of an x-ray radiation source (not shown here and assumed to be punctiform). In the following all the r-directions R are also referred to together as the r-direction R. The r-direction R is perpendicular to a z-direction Z. Perpendicular here and in particular in the following means that two directions or two surfaces or a direction and a surface are at an angle of around 90° to one another. The angle is preferably greater than 80° and smaller than 100°. In particular each of the detector surfaces 16 is perpendicular to the base plate 4 in this manner and this in turn is perpendicular to the z-direction Z. Also perpendicular to the z-direction Z is a phi-direction P, which represents a circumferential direction of an axis extending in the z-direction Z.

The module supports 10 are arranged in a recess 18 or depression incorporated in the upper face 6 of the base plate 4. It forms a fastening plane 20, which is configured so that it runs in an arc in particular parallel to the upper face 6 of the base plate 4 and in the phi-direction P. A number of drilled holes 22, 24 are incorporated in the base plate 4 following the arc and arranged in three arced rows 26, 28 in the example embodiment illustrated here. The two outer rows 26 comprise drilled holes 22, which are configured as positioning elements, while the center row 28 comprises threaded holes 24, for fastening the module supports 10 to the base plate 4 by means of a screw connection.

The base plate 4 also has a number of further through holes 30, in this instance eight, for fastening to the computed tomography system, in particular to a rotating ring of the computed tomography system. A screw for example can be passed through each of these into a thread arranged in a suitable manner on the computed tomography system. Electronic unit components 34,34', for example for evaluating signals generated by means of the detector fields 12, are also arranged on the base plate 4 and on a rear face 32 facing away from the front face 14 of the detector modules 8.

A channel 38 is also incorporated in the upper face 6 of the base plate 4 to hold a cover 36, said channel 38 running around the fastening plane 20 and a number of the electronic unit components 34 in the example embodiment illustrated here. To this end some of the segments of the channel 38 here are embodied in the phi-direction P and some in the r-direction R. In other words, the channel 38 encloses a surface in the shape of a ring sector.

Figure 2:
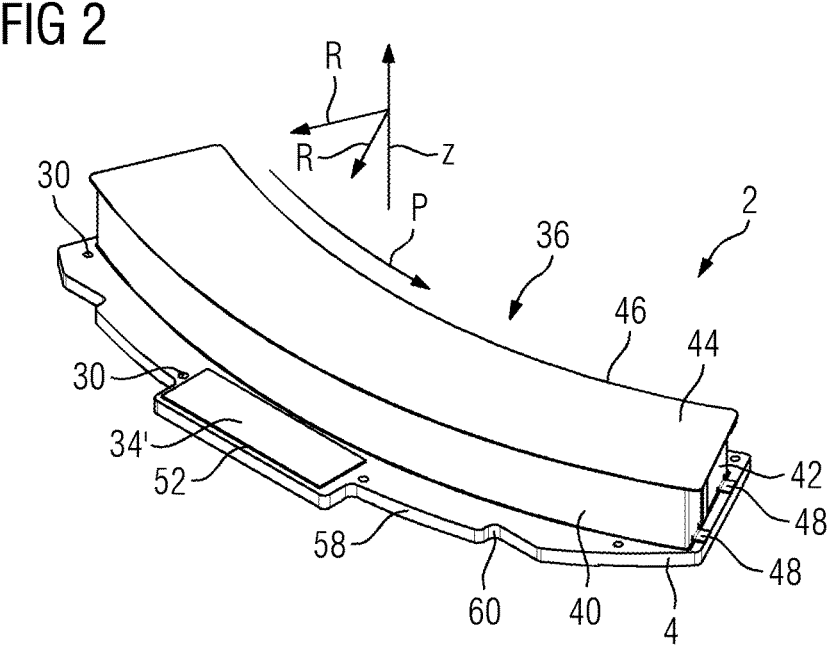
FIG. 2 shows the x-ray detector according to FIG. 1 with a cover.

The cover 36 covers a majority of the upper face 6 and is shown with the base plate 4 in FIG. 2. The cover 36 in particular comprises an in this instance continuous rear wall 40, which is arranged behind the detector surfaces 16 in the r-direction R. This means that the rear wall 40 takes up in particular unabsorbed x-ray radiation. In the example embodiment illustrated here the rear wall 40 extends in the z-direction Z from the base plate 4 and in the phi-direction P and is therefore arced. The cover 36 also comprises two side parts 42, which each extend from the base plate 4 in the z-direction Z and an r-direction R. A covering 44 is also provided, being connected to the side walls 42 and the rear wall 40. The covering 44 has a contour 46, which is arced in segments like the channel 38 and is thus tailored in particular to the rear wall 40, which runs in the phi-direction P.

The cover 36 is fastened by way of fastening elements 48 to the base plate 4 and in combination with this latter encloses a cover region 50, which is in particular also bordered by the channel 38. It is at least partially open counter to the r-direction R, in other words the cover 36 in particular does not have a continuous front wall. Instead the detector modules 8 are preferably housed here. The cover 36 is advantageously connected in a thermally conducting manner to the base plate 4, with the result that heat produced in particular by absorbed x-ray radiation can be dissipated efficiently.

In the example embodiment illustrated here, the electronic unit components 34, 34' are arranged in regions in front of (electronic unit components 34) and behind (electronic unit components 34') the rear wall 40. In front of the rear wall 40 here means the side of the rear wall 40 facing the detector modules 8, in other words in front of the rear wall 40 in the r-direction R; behind the rear wall 40 refers to the side facing correspondingly away from the detector modules 8, in other words behind the rear wall 40 in the r-direction R.

The electronic unit components 34, 34' are embodied as flat, in other words they each have the lowest possible height H in the z-direction Z. The detector surfaces 16 here are arranged at a predetermined distance A1 from the base plate 4 and the height H of the electronic unit components 34, 34' is lower than this distance A1. The electronic unit components 34, 34' also extend essentially in the r-direction R and the phi-direction P. The low height H in particular ensures that the electronic unit components 34, 34' only have a small cross section in relation to the x-ray source and are therefore exposed to as little x-ray radiation as possible.

In the example embodiment illustrated here the electronic unit components 34, 34' have a board 52 with an edge contour 54. Part of this runs in an arc for the electronic unit components 34 and it is therefore tailored in particular to the shape of the base plate 4.

FIGS. 1 and 2 in combination show that electronic unit components 34, 34' can be arranged on both sides of the rear wall 40. In particular the electronic unit component 34' arranged behind the rear wall 40 in the r-direction R is advantageously protected from x-ray radiation by the rear wall 40.

The upper face 6 of the base plate 4 is embodied as essentially planar and has in particular no curvature. In other words, apart from additional channels (for example the channel 38) and recesses, the distance A2 between upper face 6 and lower face 56 of the base plate 4 is essentially identical at every point. This means that it is possible in particular to manufacture the base plate 4 from a single plate that is of equal thickness at every point. Any channels and recesses can then be produced using a simple milling process and any drilled holes (for example the drilled holes 22, 24) can be embodied in each instance on a planar surface, which is the upper face 6 here. This simplifies the production of the x-ray detector 2 to a particular degree.

However the upper face 6 of the base plate 4 can have an at least partially arced border 58. In the example embodiment illustrated here in particular the base plate 4 is embodied in the manner of a ring sector and expediently has notches 60, for example for contact with and/or positioning on the rotating ring of the computed tomography system. In a possible alternative embodiment however the base plate 4 is embodied for example in a rectangular manner.

Figure 3:
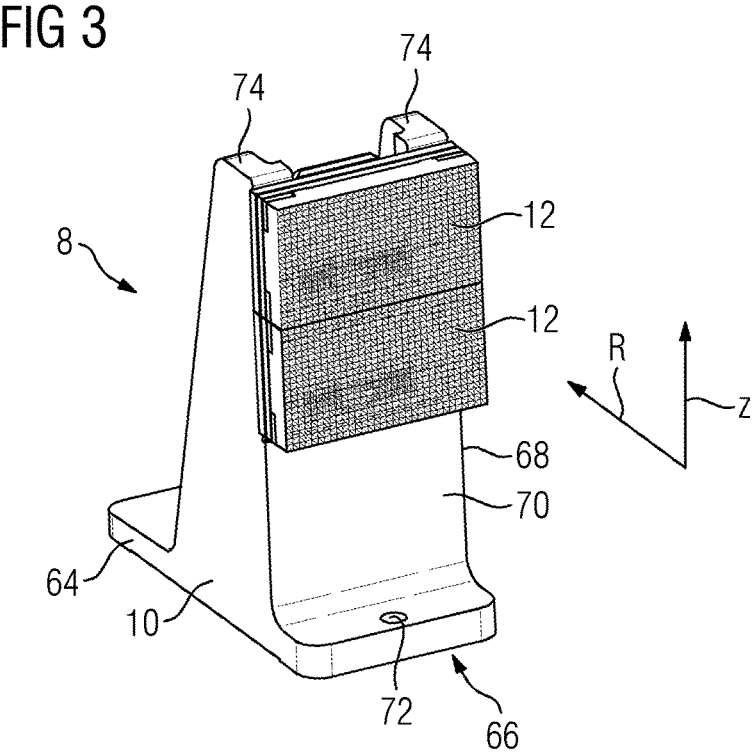
FIG. 3 shows a perspective front view of a detector module according to FIG. 1

A perspective front view of a detector module 8 is shown in FIG. 3. The detector module 8 comprises a module support 10 and a number of, in this instance two, detector fields 12. These each comprise a number of detector elements arranged in a matrix and forming a detector surface.

The module support 10 comprises a plinth 64, which has a bearing surface 66, which in the mounted state faces the upper face 6 of the base plate 4. Extending from the plinth 64 in the z-direction Z and perpendicular to the base plate 4 is a wall 68 with a wall front face 70, on which the detector fields 12 are positioned below one another. The wall 68 and plinth 64 here are arranged essentially in an L-shape. In front of the wall 68 a positioning element 72, which in the mounted state lies flush with one of the drilled holes 22 in the base plate 4 and is configured as a positioning hole, is incorporated in the plinth 64.

Two stays 74, which are connected to the plinth 64, extend along the rear face of the wall 68. This is shown particularly clearly in FIG. 4. This also shows that the stays 74 form a U-shaped profile with the plinth 64, shown here by a broken line U. In the example embodiment illustrated here the stays 74 are embodied as essentially triangular when viewed from the side, in other words they taper as the distance from the plinth 64 increases.

Figure 4:
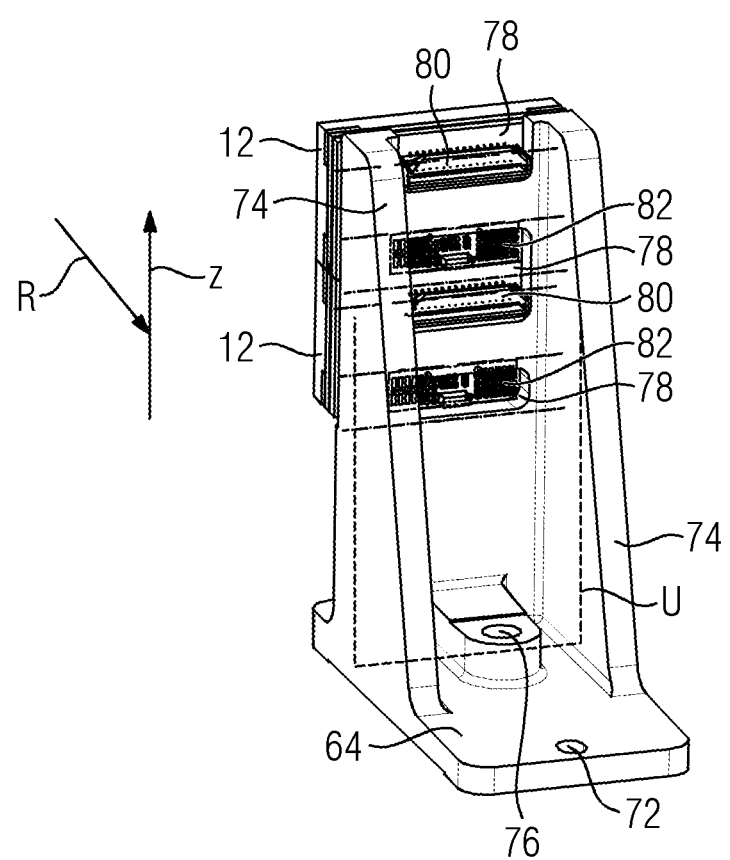
FIG. 4 shows a perspective rear view of the detector module according to FIG. 3.

Also incorporated in the plinth 64 is a fastening hole 76 for fastening the module support 10. The fastening hole 76 here is a through hole and it is associated with a drilled hole 24 (in other words a threaded hole) from the center row 28 of drilled holes 24 in the base plate 4. To produce a particularly stable connection, the plinth 64 is embodied as thicker in the region of the fastening hole 76, in other words it is higher. FIG. 4 also shows that a further positioning element 72 configured as a positioning hole is incorporated in the plinth 64.

FIG. 4 also clearly shows that a number of cutouts 78 are incorporated in the wall 68 of the module support 10 for the passage of connectors 80 of the detector fields 12. In the example embodiment illustrated here the cutouts 78 also serve to house electronic units 82 arranged on the rear faces of the detector fields 12, in particular so that they do not rest against the wall 68.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An x-ray detector for a computed tomography system, comprising:
   a base plate having an essentially planar upper surface and arcuate side surfaces, and a recess formed in the essentially planar upper surface; and
   a number of detector modules secured in the recess, each detector module including at least one detector field, that generates evaluating signals, with a detector surface facing an r-direction, each detector module including a module support fastened in the recess of the base plate, the module support including a bearing surface facing the base plate, which is perpendicular to the detector surface, for fastening purposes, wherein the detector surface is mounted on a front face of a wall of the module support facing the r-direction and at least one cutout for the passage of an electronic connector of the detector field and that houses the electronic connector, is incorporated in a rear face of the wall of the module support opposite the front face, wherein the electronic connector is introduced in the at least one cutout and the electronic connector is connectable on the rear face and/or the electronic connector is connectable to electronic components, wherein the module support includes two stays projecting from the rear face, which form a U-shaped profile with the bearing surface, and wherein the module support includes a plinth in surface contact with the base plate and the wall extends perpendicularly from the plinth, the plinth having a first thickness with a first through hole therein, and a second thickness with a second through hole within the U-shaped profile, the second thickness being thicker than the first thickness, and wherein the module supports are arranged in an arc on the base plate.

2. The x-ray detector of claim 1, wherein the module support is fastened to the base plate via a screw connection.

3. The x-ray detector of claim 1, wherein the base plate includes a number of through holes for fastening purposes.

4. The x-ray detector of claim 1, wherein a number of positioning elements are provided on the base plate and on the module support.

5. The x-ray detector of claim 4, wherein the positioning elements are drilled holes, with at least one such drilled hole in the module support lying flush with a drilled hole in the base plate.

6. The x-ray detector of claim 5, further comprising a cover covering a cover region with a rear wall, arranged on the rear face of the x-ray detector.

7. The x-ray detector of claim 6, further comprising a number of electronic unit components, arranged on the base plate and at least one of within and outside the cover region.

8. The x-ray detector of claim 4, further comprising a cover covering a cover region with a rear wall, arranged on the rear face of the x-ray detector.

9. The x-ray detector of claim 8, further comprising a number of electronic unit components, arranged on the base plate and at least one of within and outside the cover region.

10. The x-ray detector of claim 1, further comprising a cover covering a cover region that includes a channel formed in the essentially planar upper surface of the base plate.

11. The x-ray detector of claim 10, further comprising a number of electronic unit components, arranged on the base plate and at least one of within and outside the cover region.

12. An x-ray detector for a computed tomography system, comprising:
a base plate having an essentially planar surface;
a plurality of detector modules mounted on the base plate, each detector module including at least one detector field, that generates evaluating signals, with a detector surface facing an r-direction, on a front face, each detector module including a module support fastened to the surface of the base plate, the module support including a bearing surface facing the base plate, which is perpendicular to the detector surface, for fastening purposes, wherein the detector surface is mounted on a front face of a wall of the module support facing the r-direction and at least one cutout housing an electronic connector of the detector field, is incorporated in a rear face of the wall of the module support opposite the front face, wherein the electronic connector is introduced in the at least one cutout and the electronic connector is connectable on the rear face and/or the electronic connector is connectable to electronic components, wherein the module support includes two stays projecting from the rear face, which form a U-shaped profile with the bearing surface, and wherein the module support includes a plinth in surface contact with the base plate and the wall extends perpendicularly from the plinth, the plinth having a first thickness with a first through hole therein, and a second thickness with a second through hole within the U-shaped profile, the second thickness being thicker than the first thickness, wherein the module supports are arranged in an arc on the base plate, and wherein the base plate is removably attached to a rotatable ring of the computed tomography system;
a channel in the essentially planar surface of the base plate housing electronic units therein; and
a cover covering the channel.

13. The x-ray detector of claim 12, wherein the module support is fastened to the base plate via a screw connection.

* * * * *